United States Patent
Deininger et al.

(10) Patent No.: US 12,214,210 B2
(45) Date of Patent: *Feb. 4, 2025

(54) MINIMALLY INVASIVE LEADLESS NEUROSTIMULATION DEVICE

(71) Applicant: Medtronic, Inc., Minneapolis, MN (US)

(72) Inventors: Steven T. Deininger, Plymouth, MN (US); Jerel K. Mueller, Saint Paul, MN (US); Todd V. Smith, Shoreview, MN (US); Jeffrey Clayton, Zimmerman, MN (US); Thomas M. Hillebrand, Minneapolis, MN (US); Phillip C. Falkner, Minneapolis, MN (US); Jenna N. George, Edina, MN (US); Sarah J. Offutt, Golden Valley, MN (US)

(73) Assignee: Medtronic, Inc., Minneapolis, MN (US)

(*) Notice: Subject to any disclaimer, the term of this patent is extended or adjusted under 35 U.S.C. 154(b) by 119 days.

This patent is subject to a terminal disclaimer.

(21) Appl. No.: 17/485,303

(22) Filed: Sep. 24, 2021

(65) Prior Publication Data

US 2022/0096846 A1    Mar. 31, 2022

Related U.S. Application Data

(60) Provisional application No. 63/199,274, filed on Dec. 17, 2020, provisional application No. 63/198,054, filed on Sep. 25, 2020.

(51) Int. Cl.
    *A61N 1/375* (2006.01)
    *A61N 1/05* (2006.01)

(52) U.S. Cl.
    CPC ......... *A61N 1/3756* (2013.01); *A61N 1/0551* (2013.01)

(58) Field of Classification Search
    CPC ............... A61N 1/3756; A61N 1/0551; A61N 1/36007; A61N 1/375
    See application file for complete search history.

(56) References Cited

U.S. PATENT DOCUMENTS

| D337,820 S | 7/1993 | Hooper et al. |
|---|---|---|
| D350,206 S | 8/1994 | Mochida |
| (Continued) | | |

FOREIGN PATENT DOCUMENTS

| CN | 104797291 A | 7/2015 |
|---|---|---|
| CN | 104812438 A | 7/2015 |
| (Continued) | | |

OTHER PUBLICATIONS

International Preliminary Report on Patentability from related PCT Application PCT/US2021/052095, dated Mar. 28, 2023, 10 pgs.

(Continued)

*Primary Examiner* — Mark W. Bockelman
(74) *Attorney, Agent, or Firm* — Husch Blackwell LLP

(57) ABSTRACT

A leadless neurostimulation device having a header unit including at least one primary electrode having a contact surface that defines an external surface of the leadless neurostimulation device, a housing including a secondary electrode positioned on the same side of the leadless neurostimulation device as the at least one primary electrode, and a anchor device including at least one suture point for securing the leadless neurostimulation device to patient tissue or at least one protrusion nub configured to create mechanical resistance that impedes relative movement between wherein the leadless neurostimulation device and the patient tissue when implanted, where the at least one primary electrode and the secondary electrode are config- (Continued)

ured to transmit an electrical stimulation signal therebetween to provide electrical stimulation therapy to a target nerve of a patient.

23 Claims, 17 Drawing Sheets

(56) References Cited

U.S. PATENT DOCUMENTS

| | | | |
|---|---|---|---|
| 5,987,352 | A | 11/1999 | Klein et al. |
| 6,230,059 | B1 | 5/2001 | Duffin |
| 6,522,915 | B1 | 2/2003 | Ceballos et al. |
| 6,735,474 | B1 | 5/2004 | Loeb et al. |
| D523,557 | S | 6/2006 | Jones et al. |
| 7,894,907 | B2 | 2/2011 | Cowan et al. |
| 8,831,747 | B1 | 9/2014 | Min et al. |
| 9,220,911 | B2 | 12/2015 | Gordon et al. |
| 9,351,648 | B2 | 5/2016 | Mothilal et al. |
| 9,433,786 | B2 | 9/2016 | Greiner et al. |
| 9,511,236 | B2 | 12/2016 | Varady et al. |
| 9,555,246 | B2 | 1/2017 | Jiang et al. |
| 9,597,518 | B2 | 3/2017 | Deininger et al. |
| 10,238,880 | B2 | 3/2019 | Thom et al. |
| 10,328,273 | B2 | 6/2019 | Hovland et al. |
| D862,716 | S | 10/2019 | Cryan et al. |
| 10,478,612 | B2 | 11/2019 | Schepis et al. |
| D893,729 | S | 8/2020 | Joda et al. |
| D893,736 | S | 8/2020 | Yin |
| D899,610 | S | 10/2020 | Yang |
| D907,222 | S | 1/2021 | Xu |
| D908,901 | S | 1/2021 | Chen |
| D923,803 | S | 6/2021 | Ito et al. |
| 11,045,650 | B2 | 6/2021 | Brink et al. |
| D952,852 | S | 5/2022 | Deininger et al. |
| D952,853 | S | 5/2022 | Clayton et al. |
| 11,878,179 | B2 | 1/2024 | Deininger et al. |
| 2005/0288600 | A1 | 12/2005 | Zhang et al. |
| 2007/0049975 | A1* | 3/2007 | Cates ............... A61N 1/375 607/5 |
| 2008/0004535 | A1 | 1/2008 | Smits |
| 2008/0119903 | A1* | 5/2008 | Arcot-Krishnamurthy ................ A61N 1/365 607/17 |
| 2008/0195165 | A1* | 8/2008 | Stahmann ............ A61B 5/0215 607/18 |
| 2008/0243200 | A1 | 10/2008 | Scinicariello et al. |
| 2009/0082828 | A1 | 3/2009 | Ostroff |
| 2011/0301670 | A1 | 12/2011 | Gross et al. |
| 2012/0101326 | A1 | 4/2012 | Simon et al. |
| 2012/0197337 | A1 | 8/2012 | Su et al. |
| 2014/0043739 | A1 | 2/2014 | Deininger et al. |
| 2014/0163579 | A1 | 6/2014 | Tischendorf et al. |
| 2014/0344740 | A1 | 11/2014 | Kaula et al. |
| 2017/0157405 | A1 | 6/2017 | Deininger et al. |
| 2017/0224584 | A1 | 8/2017 | Greiner et al. |
| 2017/0296426 | A1 | 10/2017 | Oron et al. |
| 2019/0314635 | A1 | 10/2019 | Iyer et al. |
| 2022/0096845 | A1* | 3/2022 | Deininger ............ A61N 1/0551 |

FOREIGN PATENT DOCUMENTS

| | | |
|---|---|---|
| CN | 105492069 A | 4/2016 |
| CN | 107106841 A | 8/2017 |
| CN | 109069825 A | 12/2018 |
| CN | 11062643 A | 7/2019 |
| CN | 111447969 A | 7/2020 |
| WO | WO 2014/153219 | 9/2014 |

OTHER PUBLICATIONS

International Search Report and Written Opinion from PCT Application PCT/US2021/052095, dated Mar. 23, 2022, 18 pgs.
Application and file history for U.S. Appl. No. 29/652,586, filed Sep. 25, 2020, inventors Deininger et al.
Application and file history for U.S. Appl. No. 29/652,587, filed Sep. 25, 2020, inventors Deininger et al.
Application and file history for U.S. Appl. No. 17/485,292, filed Sep. 24, 2021, inventors Deininger et al.
Search report from related Chinese Application CN 202180071032. 9, dated Aug. 9, 2023, 10 pgs. No english translation available.
Search report from related Chinese Application CN 202180070020. 4, dated Jul. 26, 2023, 9 pgs. No english translation available.

* cited by examiner

MINIMALLY INVASIVE LEADLESS NEUROSTIMULATION DEVICE

CROSS-REFERENCE TO RELATED APPLICATIONS

This application claims the benefit of U.S. Provisional Application Ser. No. 63/198,054 filed Sep. 25, 2020, and 63/199,274 filed Dec. 17, 2020, the disclosures of which are hereby incorporated by reference in their entireties. This application is related to, but does not claim the benefit of, U.S. Provisional Application Ser. No. 63/198,053, filed Sep. 25, 2020, the disclosure of which is hereby incorporated by reference in its entirety.

TECHNICAL FIELD

The present application relates to implantable neurostimulation systems, and more specifically to minimally invasive implantable neurostimulation systems.

BACKGROUND

Implantable medical devices may be configured to deliver electrical stimulation therapy or monitor physiological signals. Electrical stimulation of nerve tissue, for example, may provide relief for a variety of disorders thereby improving the quality of life for many patients.

Some implantable medical devices (IMDs) may employ electrical leads that carry electrodes. For example, electrodes may be located at a distal portion of an elongate lead. Other examples of electrical leads may be relatively short, having one or more electrodes located along a body of the lead. Such electrical leads are provided separate from the housing or body of the IMD and coupled to the IMD during implantation to provide stimulation via the electrode at a location separated from the housing of the IMD.

Simulation of different nerve branches and clusters have been explored for treating various ailments. One avenue that has shown promising development has been the stimulation of the tibial nerve for the treatment of certain ailments such as incontinence or over-active bladder.

SUMMARY

Embodiments of the present disclosure are directed to a minimally invasive, leadless neurostimulation devices. Leadless devices do not require the use of a separate lead and instead provide a unitary structured device that may be more robust and less invasive than lead-based counterpart devices.

The disclosed devices include a housing containing components therein configured for delivering neurostimulation therapy, and an attached header unit. The header unit includes one or more primary electrodes that form a portion of the exterior and side of the header unit. The one or more primary electrodes are electrically insulated from other portions of the exterior surface of the neurostimulation device. The housing of the neurostimulation device includes a secondary electrode that operates in conjunction with the one or more primary electrodes to provide electrical simulation therapy or neuro sensing capabilities. The secondary electrode is positioned on the same side of the device as the one or more primary electrodes positioned in the header unit. The size, shape, and separation distance between the primary electrode(s) and the secondary electrode are discussed and may contribute to more effective and efficient stimulation of the tibial nerve. In some embodiments, the size, shape, and separation distance between the primary electrode(s) and the secondary electrode may be configured to produce an impedance of less than about 2,000 Ohms at the primary electrode when implanted. The device further includes a suture anchor device comprising one or more suture points.

In an embodiment, the disclosure describes a leadless neurostimulation device comprising a header unit including at least one primary electrode having a contact surface that defines an external surface of the leadless neurostimulation device, and a housing including a secondary electrode positioned on the same side of the leadless neurostimulation device as the at least one primary electrode, wherein the at least one primary electrode and the secondary electrode are configured to transmit an electrical stimulation signal therebetween to provide electrical stimulation therapy to a target nerve of a patient.

In an embodiment, the disclosure describes a leadless neurostimulation device having a header unit including at least one primary electrode comprising a contact surface that defines an external surface of the leadless neurostimulation device, a housing including a secondary electrode positioned on the same side of the leadless neurostimulation device as the at least one primary electrode, and a suture anchor device comprising at least one suture point for securing the leadless neurostimulation device to patient tissue, wherein the at least one primary electrode and the secondary electrode are configured to transmit an electrical stimulation signal therebetween to provide electrical stimulation therapy to a target nerve of a patient.

In an embodiment, the disclosure describes a leadless neurostimulation device comprising at least one primary electrode having a contact surface that defines an external surface of the leadless neurostimulation device, an outer housing that forms a side of the header unit opposite of the contact surface of the primary electrode, and a dielectric mount that receives at least a portion of the at least one primary electrode and at least partially surrounds the at least one primary electrode, the dielectric mount being configured to electrically insulate the at least one primary electrode from the outer housing, the dielectric mount being received and fixed within a recessed portion of the outer housing. The leadless neurostimulation device further comprising a housing comprising a secondary electrode positioned on the same side of the leadless neurostimulation device as the at least one primary electrode, the at least one primary electrode and the secondary electrode being configured to transmit an electrical stimulation signal therebetween to provide electrical stimulation therapy to a tibial nerve of a patient, a dielectric coating or a dielectric surface treatment that electrically insulates at least one primary electrode from the secondary electrode along an exterior surface of the device, wherein a boundary defined by the dielectric coating or the dielectric surface treatment defines the secondary electrode, and a suture anchor device comprising at least one suture point for securing the leadless neurostimulation device to patient tissue. In embodiments, the at least one primary electrode and the secondary electrode define a separation distance of about 10 mm to about 20 mm, and the leadless neurostimulation device defines a total volume of about 1.5 cubic centimeters (cc) to about 3.5 cc.

In another embodiment, the disclosure describes a method including delivering electrical simulation therapy to a tibial nerve of a patient using the disclosed leadless neurostimulation devices.

The above summary is not intended to describe each illustrated embodiment or every implementation of the subject matter hereof. The figures and the detailed description that follow more particularly exemplify various embodiments.

BRIEF DESCRIPTION OF DRAWINGS

The disclosure can be more completely understood in consideration of the following detailed description of various embodiments of the disclosure, in connection with the accompanying drawings, in which.

Figure 1A:
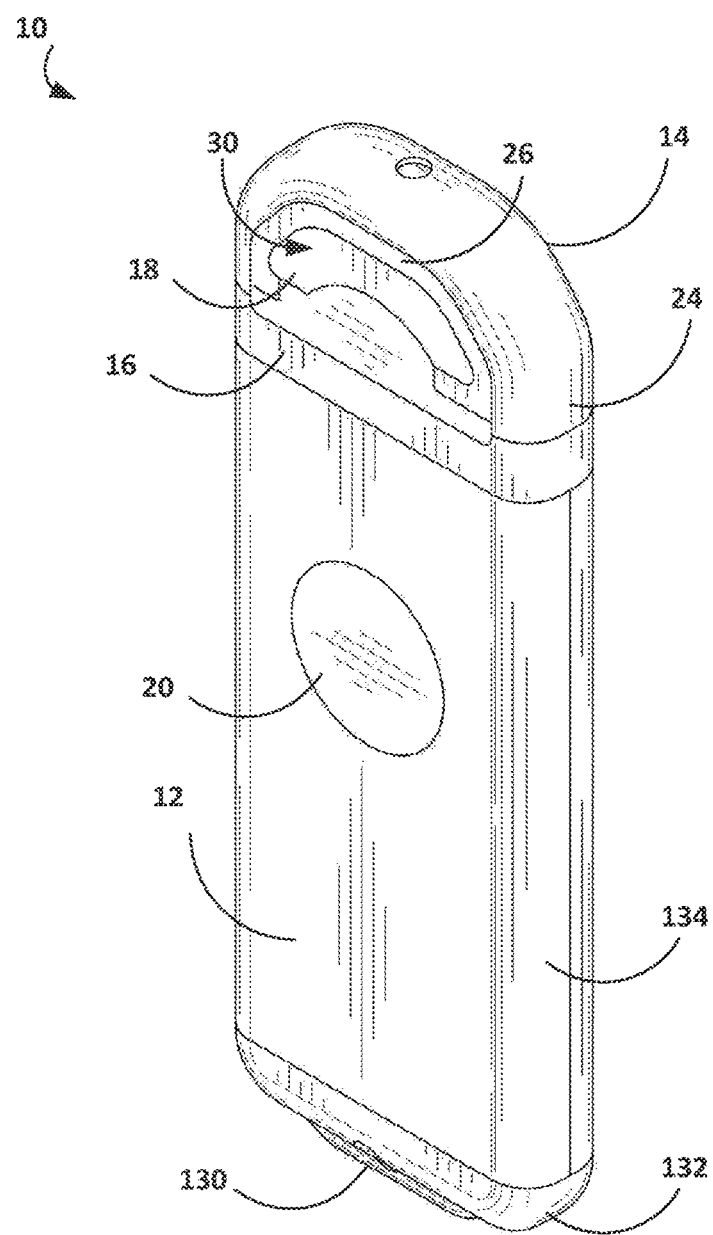
FIGS. 1A and 1B are schematic perspective views showing an example leadless neurostimulation device as described herein.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Embodiments of the leadless neurostimulation devices described herein may be useful for numerous types of neurostimulation therapies, such as for pain control, autonomic nervous system modulation, functional electrical stimulation, tremors, and more. In preferred embodiments, the leadless neurostimulation devices described herein may be useful for stimulating one or more nerves to control symptoms of overactive bladder, urgency frequency, nocturia, painful bladder syndrome, chronic pelvic pain, incontinence, or other pelvic health conditions. These embodiments may also be useful for stimulating one or more peripheral nerves to control pain in one or more areas of the body, such as a foot, ankle, leg, groin, shoulder, arm, wrist, or the back, for example. In one example, embodiments of the disclosed leadless neurostimulation devices may be used to stimulate a tibial nerve of a patient.

Figure 1B:
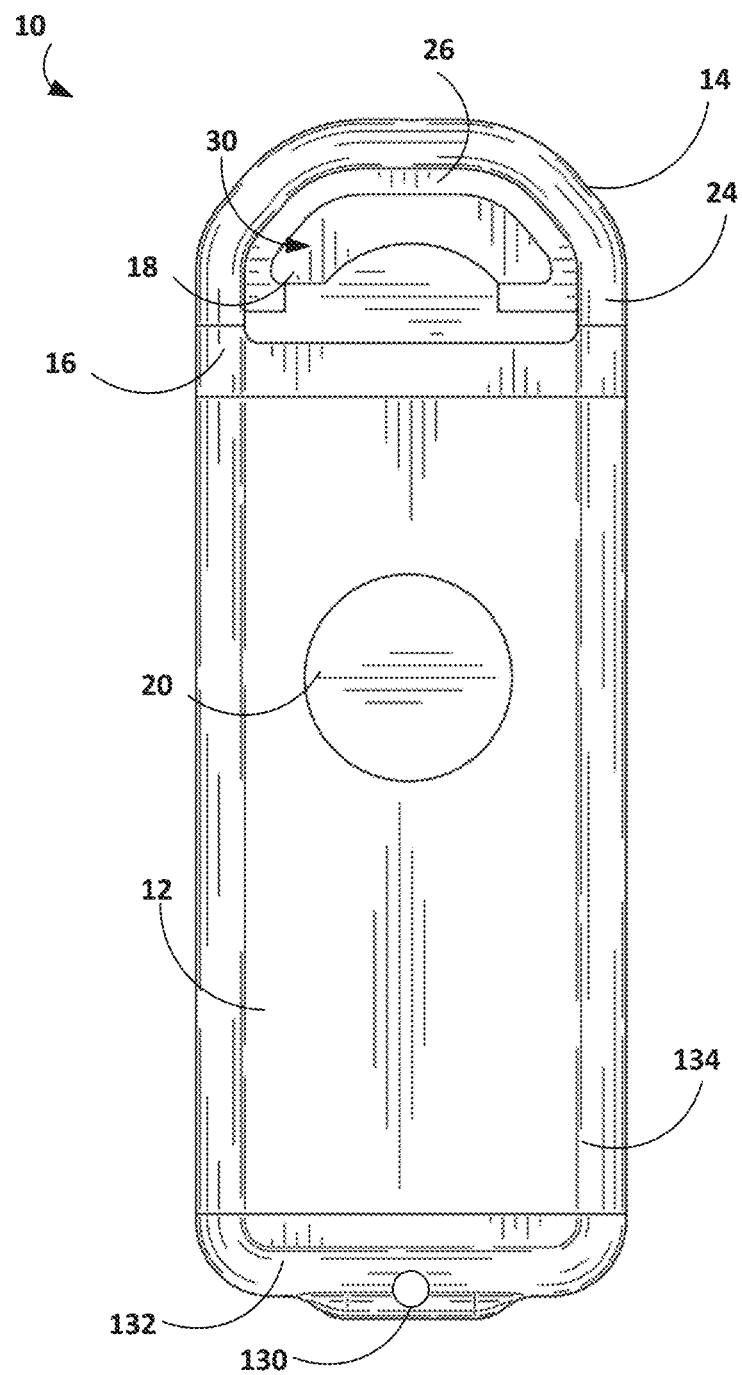
Figure 2A:
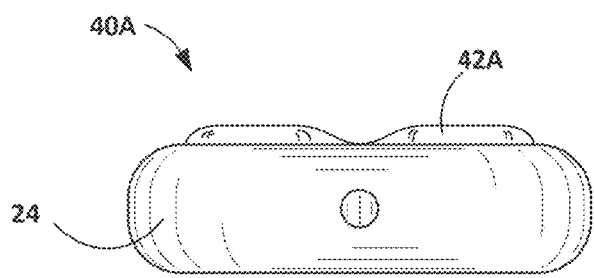
FIGS. 2A-2E are schematic side views of example header units that may be used with the device of FIGS. 1A and 1B.
Figure 2B:
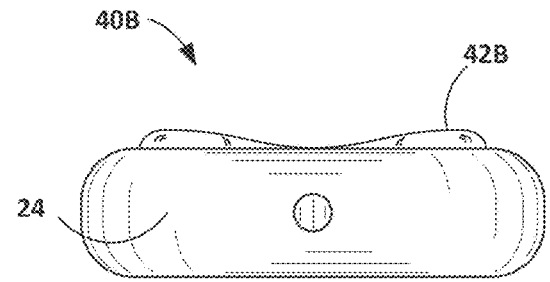
Figure 2C:
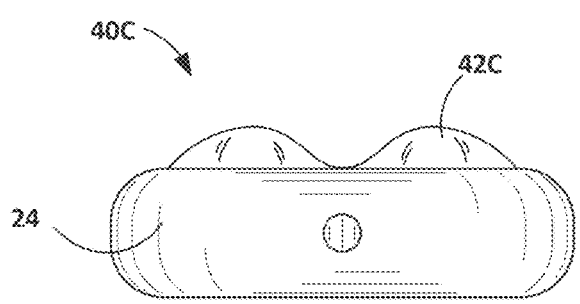
Figure 2D:
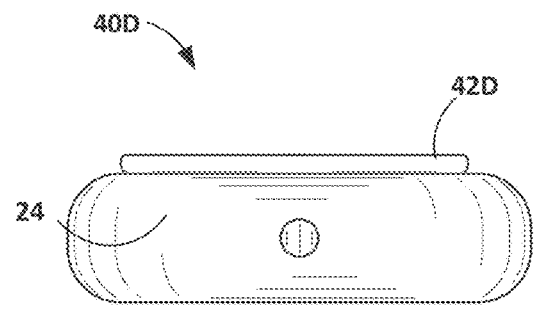
Figure 2E:
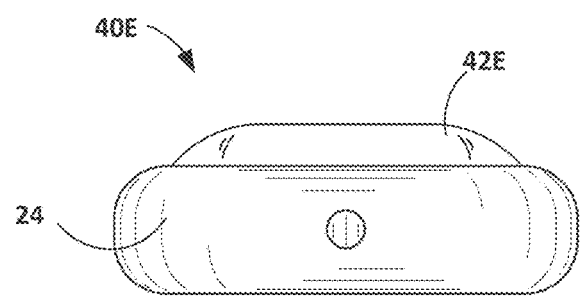
Figure 3A:
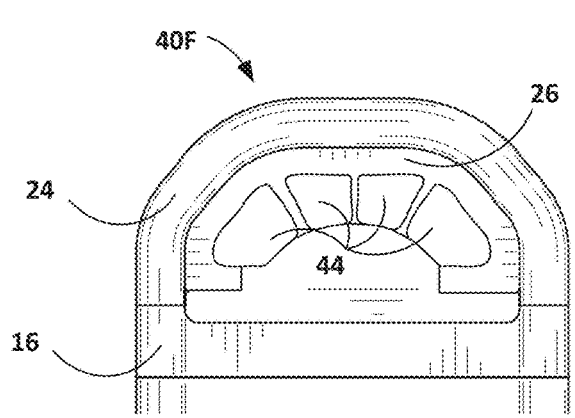
FIGS. 3A-3E are schematic views of example header units that include a plurality of primary electrodes that may be used with the leadless neurostimulation device of FIGS. 1A and 1B or with the header unit and electrode arrangements of FIGS. 2A-2E.
Figure 3B:
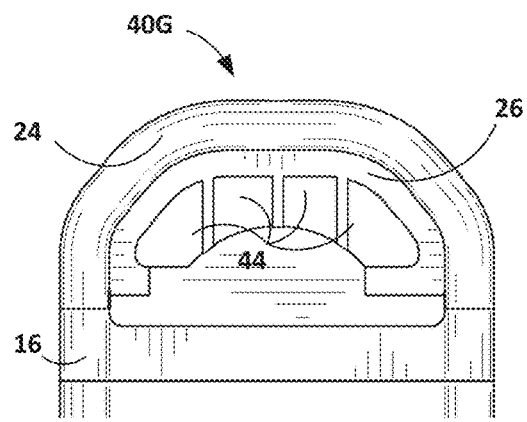
Figure 3C:
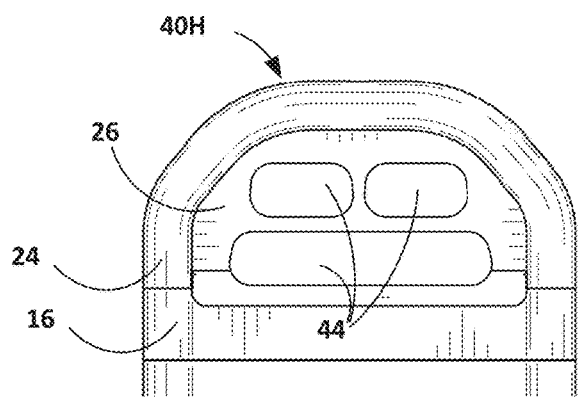
Figure 3D:
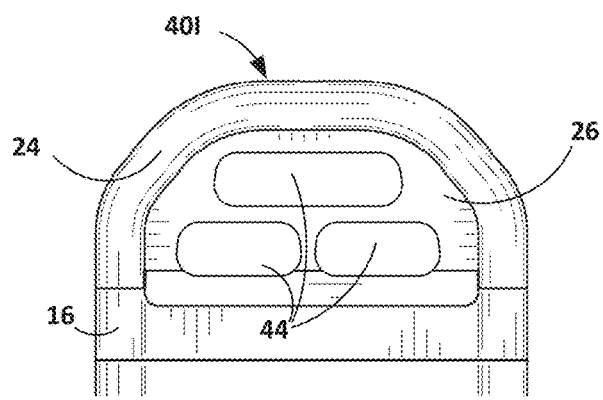
Figure 3E:
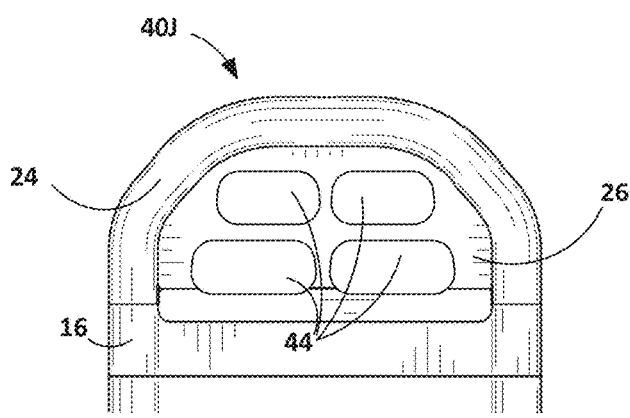

FIGS. 1A and 1B are schematic perspective views showing an example leadless neurostimulation device 10. Leadless neurostimulation device 10 includes a housing 12 containing components therein configured for delivering neurostimulation therapy, a header unit 14 that includes one or more primary electrodes 18, and a mounting plate 16 that couples housing 12 to header unit 14. Header unit 14 includes at least one primary electrode 18 that forms part of an exterior surface of header unit 14. Housing 12 includes a secondary electrode 20 that forms part of an exterior surface of housing 12 and is positioned on the same side of device 10 as primary electrode 18. In an alternate embodiment not depicted, primary electrode 18 and secondary electrode 20 may be arranged on opposite sides of device 10. Primary electrode 18 and secondary electrode 20 operate in conjunction with one another to provide stimulation therapy to a target treatment site (e.g., a tibial nerve). Secondary electrode 20 may also be referred to as a case electrode, can electrode, or reference electrode. In an embodiment, primary electrode 18 may comprise a cathode and secondary electrode 20 may comprise an anode. In some embodiments, primary and secondary electrodes 18 and 20 may be characterized as a bipolar system.

The terms "primary" and "secondary" are used to differentiate two or more electrodes that are configured to transmit an electrical signal therebetween. The terms are not used to imply a hierarchy among the electrodes, positive and negative terminal, a total number of electrodes, or a directionality by which a signal is transmitted between the electrodes.

Header unit 14 includes outer housing 24, primary electrode 18, and dielectric mount 26. Outer housing 24 is coupled to mounting plate 16 and may define a partially recessed cavity that receives dielectric mount 26 and primary electrode 18. Outer housing 24 and mounting plate 16 may be made of metal or metal alloy (e.g., titanium or titanium alloy) to allow for easy coupling there between (e.g., laser welding) as well as allow for the coupling of mounting plate 16 to housing 12. Additionally, or alternatively, outer housing 24 or mounting plate 16 may be composed of a ceramic material, or non-conductive plastic material (e.g., polypropylene) including appropriate mechanisms (e.g., metal inserts) for coupling outer housing 24 to mounting plate 16.

In some embodiments, the seam between mounting plate 16 and outer housing 24 may form at least a partial hermetic seal. In an alternate embodiment not depicted, header unit 14 may be configured so as to be coupleable directly to housing 12, without the need for a separate mounting plate element.

Primary electrode 18 defines exterior contact surface 30 configured to be brought into direct contact with tissue of the patient. Contact surface 30 may also form a portion of a side of header unit 14, which is preferably on the same side of device 10 as secondary electrode 20.

The exterior perimeter of contact surface 30 is at least partially bordered by dielectric mount 26, which may also form a portion of the exterior surface of header unit 14 absent of the dielectric coating disclosed below. Dielectric mount 26 electrically insulates and physically separates primary electrode 18 from outer housing 24, mounting plate 16, and other portions of device 10. Additionally, or alternatively, dielectric mount 26 may be molded around primary electrode 18 using silicone or liquid silicone rubber LSR, for example, to help physically retain primary electrode 18 within header unit 14 of device 10. In some embodiments, dielectric mount 26 may be formed integrally with outer housing 24 provided the components are formed of a non-conductive material.

Outer housing 24 may form the majority of the body of header unit 14. In particular, outer housing 24 forms the side of header unit 14 opposite of contract surface 30, the perimeter edges (apart from the contact surface provided with mounting plate 16), and a portion of the same side of header unit 14 as contact surface 30 of primary electrode 18. In some embodiments, outer housing 24 may have a rounded, semi-circular, or D-shaped perimeter edge that provides a relatively smooth surface without any abrupt or sharp edges or lines than may present an irritation to the patient after implantation. In some embodiments, outer housing 24 is configured to receive and form a partial shell around dielectric mount 26. As such, outer housing 24 may define a concave interior surface (not shown) that receives a portion of dielectric mount 26. Dielectric mount 26 may be secured to outer housing 26 using a suitable adhesive material (e.g., non-conductive medical adhesive, epoxy volcanized silicone, or the like).

Primary electrode 18 may be of suitable shape to provide electrical stimulation to the tibial nerve through the fascia layer of a patient. In some embodiments, contact surface 30 of primary electrode may be substantially flat (e.g., flat or nearly flat) as shown in FIG. 1A. Alternatively, primary electrode 18 may define a curved surface (e.g., a semi-cylindrical shape or other 2D or 3D curved plane) that helps primary electrode 18 follow the curvatures of the fascia layer of a patient when implanted to provide better contact and focusing of the electrical signal directed to the tibial nerve. The curved surface may extend over the entirety of contact surface 30, or only over a portion of the surface. Additionally, or alternatively, the curvature may be confined to only contact surface 30 of primary electrode 18, or may extend over other portions of device 10 such as other parts of header 14, mounting plate 16, or housing 12. By including the curvature over other portions of device 10, the device may provide a more ergonomic fit when implanted while also helping to direct the stimulation signal to the tibial nerve.

In some embodiments, contact surface 30 of primary electrode 18 may also protrude from the plane defined by housing 12. Such a protrusion may help apply additional pressure to the fascia of the patient and help guide the electrical stimulation signal deeper into the tissue of the patient. Primary electrode 18 may also define one or more interlocking features, carveouts, recesses, or other structures that reduce the overall volume of primary electrode 18 without interfering with contact surface area 30. The reduced volume and interlocking features may also help reduce manufacturing costs as well as help fix primary electrode 18 relative to dielectric mount 26.

FIGS. 2A-2E are schematic side views (top-down) of example header units 40A-40E that may be used with device 10 of FIGS. 1A and 1B. Each header unit 40A-40E includes one or more primary electrodes 42A-42E that may be curved, protrude away from the plane defined by housing 12, or both. The curvatures shown in FIGS. 2A-2C and 2E generally curve relative to the centerline defined by device 10 (e.g., into the page in FIGS. 2A-2C and 2E through the center of the device) to help focus the electrical stimulation to a line substantially parallel (e.g., parallel or nearly parallel) to the center line of device 10. Additionally, or alternatively, by protruding primary electrodes 42A-42E, the electrode may lie in closer proximity to the tibial nerve compared to secondary electrode 20 which can help guide or steer the electrical stimulation to the nerve allowing for deeper nerve stimulation (e.g., stimulation of tibial nerve with deep or anterior/posterior tracks).

Primary electrode 18 may be formed using any suitable material capable of delivering electrical stimulation therapy to the patient once implanted. Such materials may include, but are not limited to titanium, titanium alloy, platinum iridium, or the like. In preferred embodiments, at least contact surface 30 is formed of platinum iridium, which provides low impedance to bodily tissue (e.g., electrode-tissue interface). The body of primary electrode 18 may be made of the same or different material than contact surface 30. For example, primary electrode 18 may be formed of titanium with contact surface 30 formed of platinum iridium. Using platinum iridium or titanium may be beneficial in reducing or eliminating the potential for charge buildup on the external surface of device 10 during operation.

Additional details discussing possible structures and arrangements of header unit 14 and the various components included therein are disclosed in provisional application Ser. No. 63/198,053, entitled "MINIMALLY INVASIVE LEADLESS NEUROSTIMULATION DEVICE," incorporated by reference above.

Header unit 14 is coupled to mounting plate 16 and likewise mounting plate 16 is coupled to housing 12. Housing 12 includes secondary electrode 20. In some embodiments, secondary electrode 20 may be defined by an area of the body of housing 12. For example, housing 12 may be formed of a metallic material (e.g., titanium) and electrically coupled to the processing circuitry of leadless neurostimulation device 10. The outer surface of housing 12, including portions of mounting plate 16 and header unit 14, may be coated with a dielectric material apart from the surface area that defines secondary electrode 20 and primary electrode 18. The dielectric material may at least partially encapsulate device 10 such that the boundary created by the dielectric material define the area of secondary electrode 20, contact surface 30, or both.

The dielectric coating may be applied using any suitable technique. In some such examples, the areas defining contact surface 30 and secondary electrode 20 may be masked with a suitable material such as tape. Leadless neurostimulation device 10 may be then coated using vapor deposition, dip coating, spray coating of similar technique with an adherent dielectric material followed by subsequent removal of the mask material to expose the surfaces of contact surface 30 and secondary electrode 20.

Suitable dielectric materials for coating leadless neurostimulation device 10 may include, but are not limited to, parylene, LSR, or silicone. Additionally, or alternatively, the outer surface of neurostimulation device 10 or portions thereof, may include a surface treatment such as an anodization treatment to modify portions of the surface to make the surface non-conductive. For example, portions of housing 12, outer housing 24, or both, if made of metal (e.g., titanium) may be treated through anodization to make select surfaces non-electrically conductive. In such examples, for purposes of this disclosure the exterior surface of the components may still be characterized as being metal (e.g., titanium) although the component has received such surface treatment.

In preferred examples, the outer surface of leadless neurostimulation device 10 may be formed primarily of parylene. Formation of the desired electrode profiles may utilize dielectric blocking methods (e.g., use of a masking material during manufacture) or dielectric removal methods (e.g., removal via laser or soda blast) without damaging the dielectric coating.

In some embodiments, the dielectric coating may also contribute to creating a hermetic seal around leadless neurostimulation device 10. The general configuration of attaching header 14 and housing 12 respectively to mounting plate 16 may also produce a hermetic seal within device 10. Coating device 10 with a dielectric material possessing sealing properties such as parylene, LSR, or silicone may either provide additional robustness to the hermetic seal of device. Providing leadless neurostimulation device 10 in a hermetically sealed form may contribute to the device's long-term functionality thereby providing advantages over other non-hermetically sealed devices.

The processing circuitry and components of neurostimulation device 10 are contained within housing 12. Examples of such processing components may include one or more electronic circuits for delivering electrical stimulation therapy, telemetry hardware, power supply, memory, processor(s). Housing 12 can also include communication circuitry disposed therein for receiving programming communication from an external programmer, or providing feedback to a programmer or other external device.

In one example, housing 12 can include an energy source enclosed therein, e.g., a rechargeable or non-rechargeable battery. In another example, leadless neurostimulator 10 can also be configured to receive energy signals from an external device and transduce the received energy signals into electrical power that is used to recharge a battery of the device, an energy source e.g., a battery, processing circuitry, and other necessary components enclosed therein. In some embodiments, device 10 can be configured to receive energy signals from an external device and transduce the received energy signals into electrical power that is used to recharge a battery of device 10. Additionally, or alternatively device 10 may include a non-rechargeable primary cell battery.

In some embodiments, housing 12 of leadless neurostimulation device 10, and its various processing components may be substantially similar to the housing portion of the InterStim Micro Neurostimulator available from Medtronic. The InterStim Micro Neurostimulator may be modified to receive header unit 14 described herein along with modifications to provide secondary electrode 20. The total volume of neurostimulation device 10 may be relatively small as well. 0.5 cubic centimeters (cc) to about 6 cc, about 1.5 cc to about 3.5 cc, or about 2 cc to about 3 cc.

The size, shape, and physical separation distance between primary electrode 18 and secondary electrode 20 can affect the functionality and effectiveness of leadless neurostimulation device. In some embodiments, primary electrode 18 may define a contact surface area of about 5 $mm^2$ to about 90 $mm^2$. In preferred embodiments that include only a single primary electrode 18, the contact surface area may be greater than about 10 $mm^2$, greater than about 15 $mm^2$, greater than about 18 $mm^2$, greater than about 20 $mm^2$, less than 35 $mm^2$, less than 30 $mm^2$, and less than 25 $mm^2$. Secondary electrode 20 may define a contact surface area of about 5 $mm^2$ to about 120 $mm^2$ or about 40 $mm^2$ to about 120 $mm^2$. However, devices having larger sized secondary electrodes may increase the minimal current needed to create a therapeutic response. The separation distance between primary electrode 18 and secondary electrode 20 may be about 5 mm to about 15 mm.

In some embodiments, the size, shape, and physical separation distance between primary electrode 18 and secondary electrode 20 may be configured such that primary electrode 18 has an impedance of less than 2,000 ohms (e.g., between about 250 ohms and 1,000 ohms) when implanted. Additionally, or alternatively, primary and secondary electrodes 18 and 20 may be arranged in a non-concentric arrangement such that one electrode does not substantially encircle the other.

In some embodiments, header unit 14 may include a plurality of primary electrodes 18. FIGS. 3A-3E are schematic views or example header units 40F-40J that each include a plurality of primary electrodes 44. In some embodiments primary electrodes 44 may be similarly sized and shaped or include a collection of differently shaped and sized electrodes.

In preferred embodiments, header unit 14 may include one or more primary electrodes 42. The inclusion of more than one primary electrode in device 10 may increase functionality and precision of device 10. For example, one or more of primary electrodes 42 may be configured to operate in one or more modes including one or more sensing modes where, for example, the electrode is used to detect measurable feedback from the tibial never (e.g., sensed activity or the nerve prior to or after stimulation) or sense the relative location of the tibial nerve to optimize stimulation and a delivery mode where the electrode delivers stimulation therapy to the tibial nerve. The processing circuitry may select one or more optimal primary electrodes 44 based on proximity to the tibial nerve for the delivery of stimulation therapy so as to steer the stimulation field. Additionally, or alternatively, in a sensing mode, one or more of primary electrodes 42 may be configured to monitor the activity of the tibial nerve or adjacent tissue prior to or during the delivery of simulation therapy to determine if sufficient therapy has been delivered. The sensory mode may be actuated by processing circuitry contained in the body of housing 12.

In some embodiments, having multiple primary electrodes may improve stimulation targeting which could limit possible side effects from stimulating unintended areas. Improved targeting may also allow for reduced stimulation amplitudes which could improve battery longevity. Multiple primary electrodes may also provide unique therapy applications (e.g., providing stimulation to two sides of the nerve simultaneously) using one or multiple wave forms. Additionally, or alternatively the sensing technologies could be used to optimize stimulation (e.g., determine when to apply stimulation and when it is not needed, adjust parameters of the stimulation such as amplitude, voltage, or the like).

Figure 4A:
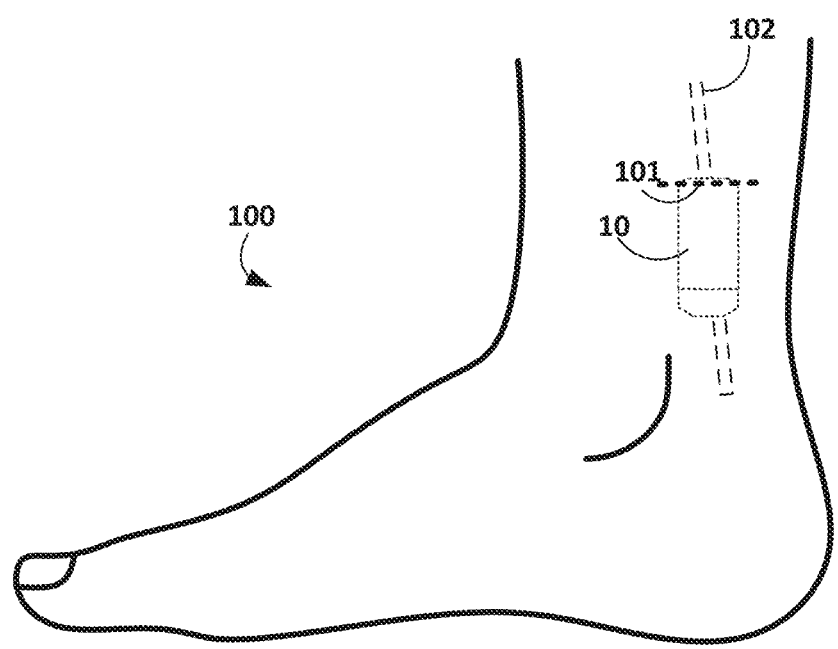
FIG. 4A is a side view of a patient's leg showing the leadless neurostimulation device of FIGS. 1A and 1B implanted in a patient's leg near the tibial nerve.
Figure 4B:
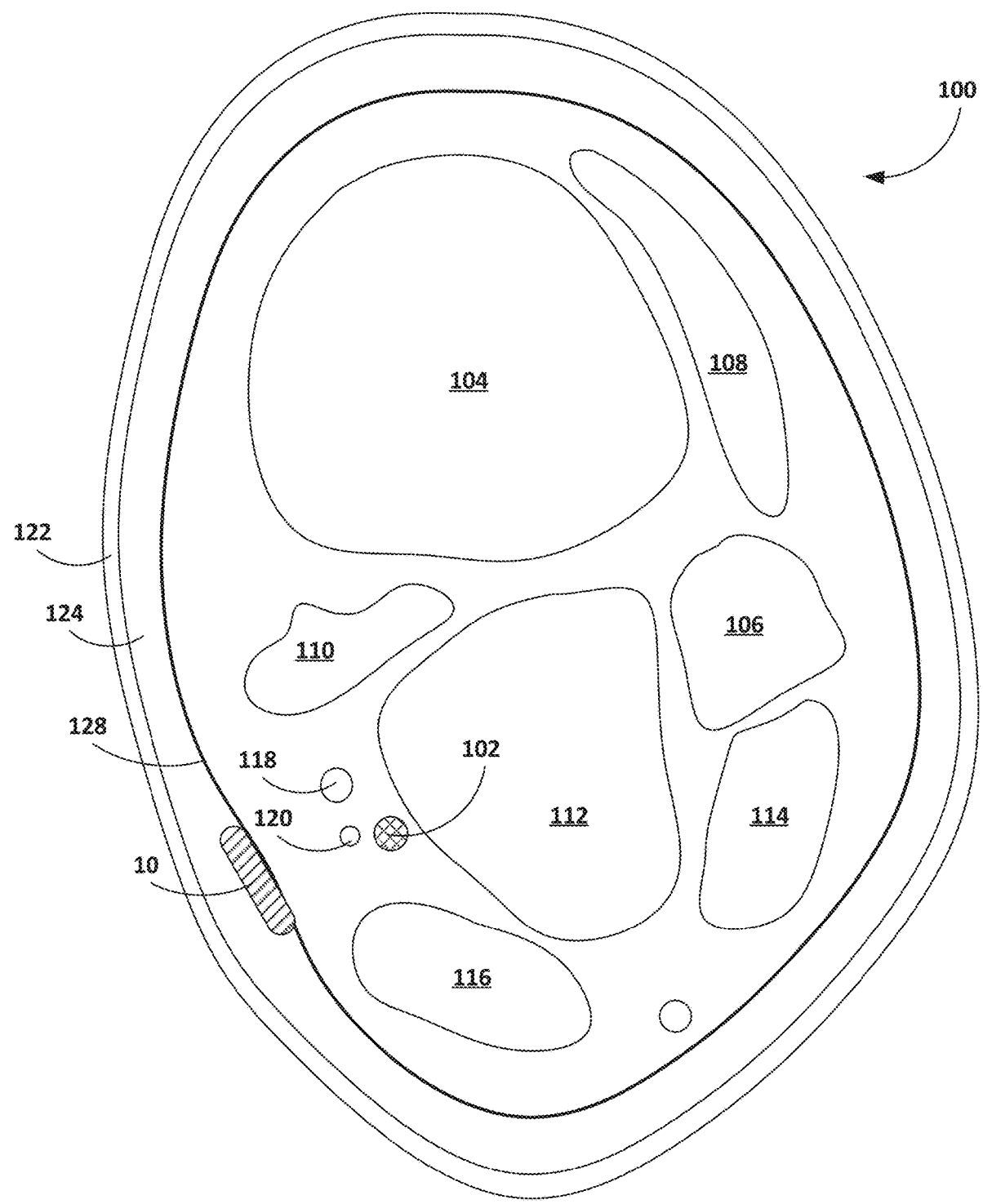
FIG. 4B is a cross-sectional view of a patient's leg showing the leadless neurostimulation device of FIGS. 1A and 1B implanted near the patient's tibial nerve.

Referring now to implantation, FIG. 4A is a side view of a patient's leg 100 showing the leadless neurostimulation device 10 of FIGS. 1A and 1B implanted and FIG. 4B shows a cross-sectional schematic view of leadless neurostimulation device 10 implanted in leg 100 of a patient near the ankle adjacent to the tibial nerve 102. The cross section of leg 100 illustrates tibia 104, fibula 106, fibularis tertius 108, flexor digitorum longus 110, flexor hallucis longus 112, fibularis brevis 114, soleus 116, posterior tibial artery 118, posterior tibial vein 120, skin 122, cutaneous fat layer 124, and fascia layer 128. Device 10 can be implanted through skin 122 and cutaneous fat layer 124 via a small incision 101 (e.g., about one to three cm) above the tibial nerve on a medial aspect of the patient's ankle. While incision 101 is shown approximately horizontal to the length of the tibial nerve, other incisions or implantation techniques could be used according to physician preference.

Device 10 may be positioned adjacent to the region defined by flexor digitorum longus 110, flexor hallucis longus 112, and soleus 116 in which tibial nerve 102 is contained and implanted adjacent and proximal to fascia layer 128 with primary electrode 18 and secondary electrode 20 facing toward tibial nerve 102. Incision 101 preferably does not cross fascia layer 128 thereby reducing the risk of complications with the surgical procedure. In an embodiment, leadless neurostimulation device 10 may be implanted such that primary electrode 18 is oriented inferiorly relative to secondary electrode 20.

Optional testing of leadless neurostimulation device 10 may be performed to determine if device 10 has been properly positioned in proximity to tibial nerve 102 to elicit a desired response from an applied electrical stimulation. In an example, device 10 is controlled by an external programmer to deliver test stimulation, and one or more indicative responses are monitored, such as toe flexion from simulation of the tibial motor neurons controlling the flexor hallucis brevis or flexor digitorum brevis, or a tingling sensation in the heel or sole of the foot excluding the medial arch. If such testing does not elicit appropriate motor or sensory responses, the practitioner may reposition device 10 and retest.

Once a practitioner has determined device 10 is properly positioned to provide an appropriate patient response to delivered stimulation therapy, housing 12 can be secured in place if needed. The natural shape of the region in which device 10 is implanted, and the shape of device 10 itself has shown good compatibility with the surrounding tissue depending on the patient body type to help prevent device 10 from shifting or rolling after implantation. However, leadless neurostimulation device 10 may further include one or more anchoring devices to help secure device 10 to fascia 102 or other parts of leg 100.

FIGS. 1A and 1B illustrate one example type of anchoring mechanism on device 10 which include a suture anchor 130 at the distal end of housing 12, opposite of the end attached to mounting plate 16. Suture anchor 130 may include one or more apertures formed into the end cap 132 of housing 12, which is welded to tubular body 134 such that the end cap 132 and body 134 collectively form housing 12.

The construction of suture anchor 130 within end cap 132 provides a compact construction for device 10 allowing for the overall device volume to remain low. However, as end cap 132 can be made of a metallic or ceramic and fixed relative to body 134 during assembly, the design of suture anchor including the number of apertures their orientation is fixed during manufacturing of device 10. Certain suture anchor designs may be optimized for specific procedures (e.g., tibial nerve stimulation) but may be less preferred in other applications.

Figure 5:
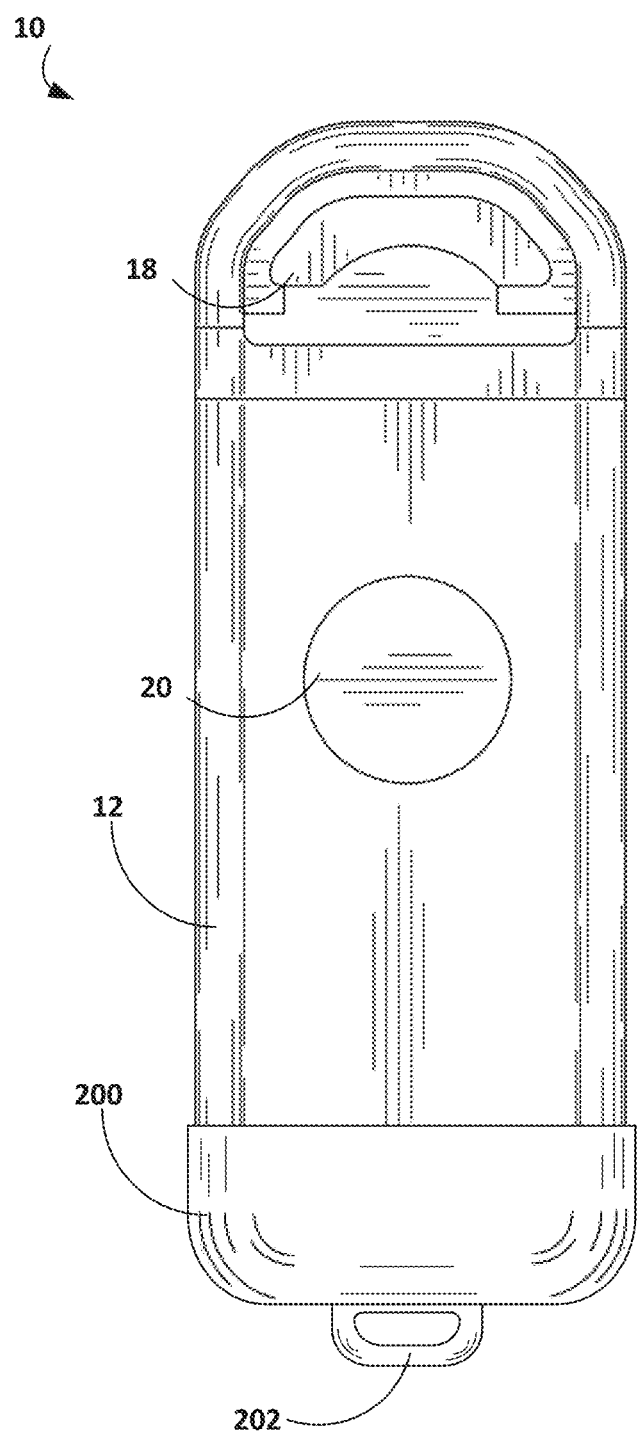
FIG. 5 is a schematic perspective view of a suture anchor device that can be used with the disclosed neurostimulation device.

FIG. 5 is a schematic perspective view of a suture anchor device that can be used with neurostimulation device 10. The suture anchor device is in the form of a flexible anchor endcap 200 that can fit over the distal end of housing 12 (e.g., over endcap 132 with suture point 130 excluded). Endcap 200 may define a cup shape that receives housing 12 and secures housing 12 in place. In some embodiments, flexible anchor endcap 200 may be modular relative to housing 12 (e.g., secured via compression fit) or may be fixed to housing 12.

Endcap 200 may include one or more suture points 202 used by the clinician to secure device 10 to the surrounding tissue (e.g., fascia 102 or other parts of leg 100 in tibial nerve stimulation therapy). Suture point 202 may be centered along one or more axes of device 10 as shown in FIG. 5 or may be asymmetrically positioned toward one side or face of device 10 (e.g., positioned so that suture point 202 is mounted more toward the same or opposite side of housing 12 containing secondary electrode 20). In some embodiments, the aperture of suture points 202 may face parallel to the direction of secondary electrode 20. In other embodiments, the aperture of suture points 202 may face perpendicular to the direction of secondary electrode 20 or at some other angle.

Endcap 200 may be composed of an elastomeric material. Example materials may include silicone or liquid silicone rubber. In some embodiments, endcap 200 may be provided separate (unattached) from device 10 and attached by the clinician during implantation either by compression fit (e.g., force generated by the elastomeric material of endcap 200) or with a medical adhesive. Having anchor endcap 200 be modular may allow the clinician to select a specific endcap design at the time of implantation to best conform or secure to the surrounding tissue at the site of implantation.

Figure 6:
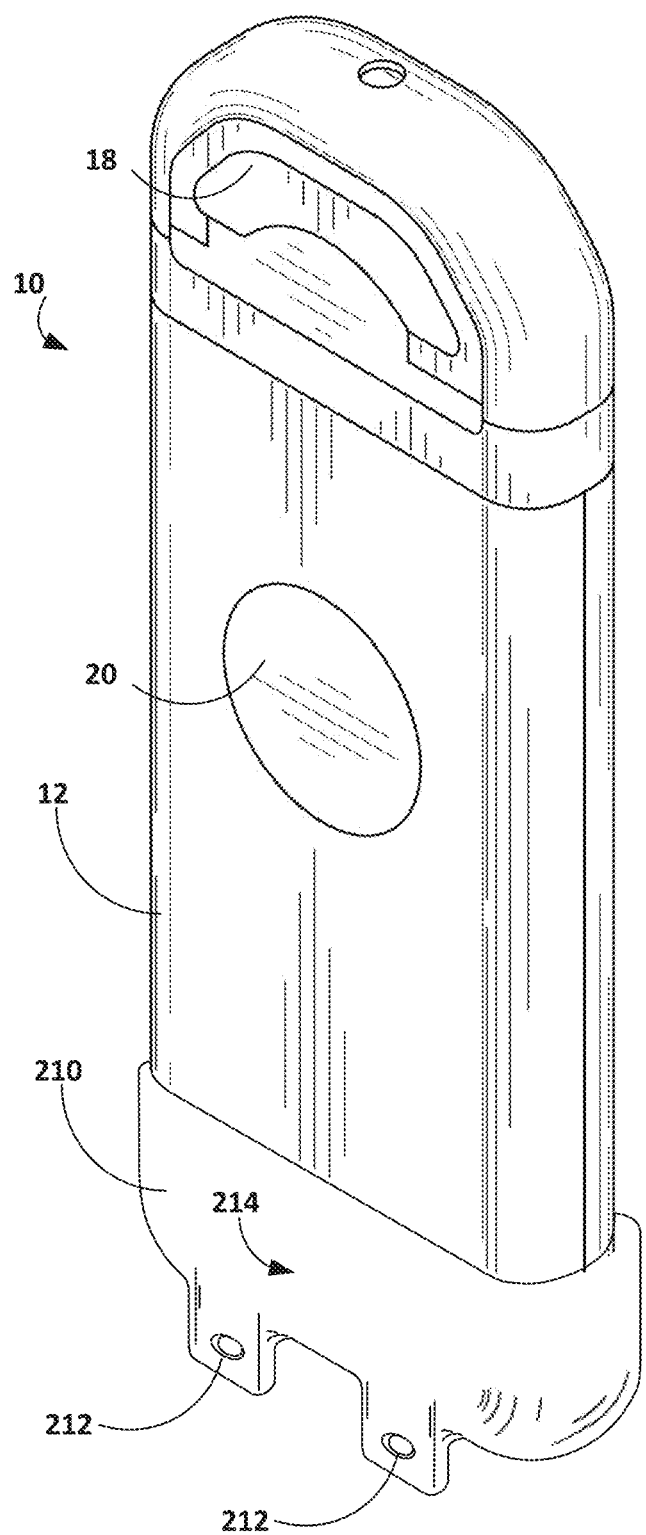
FIG. 6 is a schematic perspective view of another design for a suture anchor device that can be used with the disclosed neurostimulation device.

FIG. 6 is a schematic perspective view of another suture anchor design that can be used with neurostimulation device 10. The suture anchor includes a flexible anchor endcap 210 that can fit over the distal end of housing 12. Endcap 210 is substantially the same as endcap 200 but is shown with a plurality of suture points 212. Each suture point 212 is set toward the same side of housing 12 as second electrode 20. For example, suture points 212 may set flush with side 214 of the suture anchor device that is the same as the side of housing 12 containing secondary 20. However, due to the thickness of endcap 210, suture points 212 may not be considered flush relative to secondary electrode 20. Setting suture points 212 toward the same side of housing 12 as second electrode 20 may provide a flush mount of endcap 210 against the target tissue (e.g., fascia 102) as compared to other designs where the suture points are more centrally aligned (e.g., as shown in FIG. 5).

Figure 7:
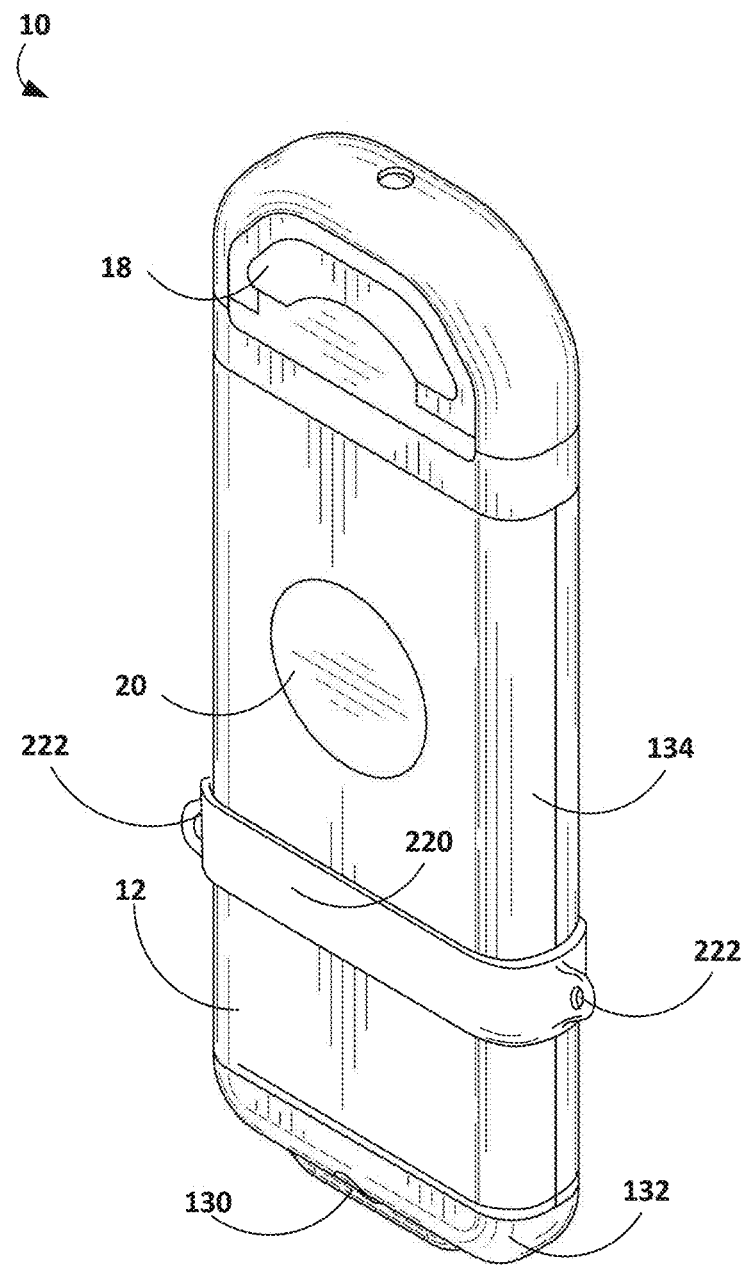
FIG. 7 is a schematic perspective view of another design for a suture anchor device that can be used with the disclosed neurostimulation device.

FIG. 7 is a schematic perspective view of another suture anchor that can be used with neurostimulation device 10. Device 10 includes a flexible anchor band 220 that can fit around housing 12 (e.g., around tubular body 134). Anchor band 220 includes a pair of suture points 222 positioned at the two sides adjacent to the side of housing 12 that includes secondary electrode 20. Suture points 222 provide a convenient means of securely anchoring device 10 at two opposing sides to the surrounding tissue without interfering with the neurostimulation therapy.

Flexible band 220 may be composed of an elastomeric material (e.g., silicone or liquid silicone rubber). Flexible band 220 may be fixed to housing 12 or may be movable relative to housing 12. Having flexible band 220 be movable relative to housing 12 may allow the clinician to reposition band 220 at the time of implantation of device 10 to provide the best anchoring position for anchor points 222 relative to the patient's tissue. While, movable, flexible band 220 may still provide a compression fit to housing 12 to provide a secure fit with the device, thus preventing migration or unintended to movement of band 220 relative to housing 20. Endcap 132 of device 10 may optionally include suture point 130 for an additional attachment point. Further, the disclosed suture anchor devices may be used alone or in combination with one another.

Figure 8:
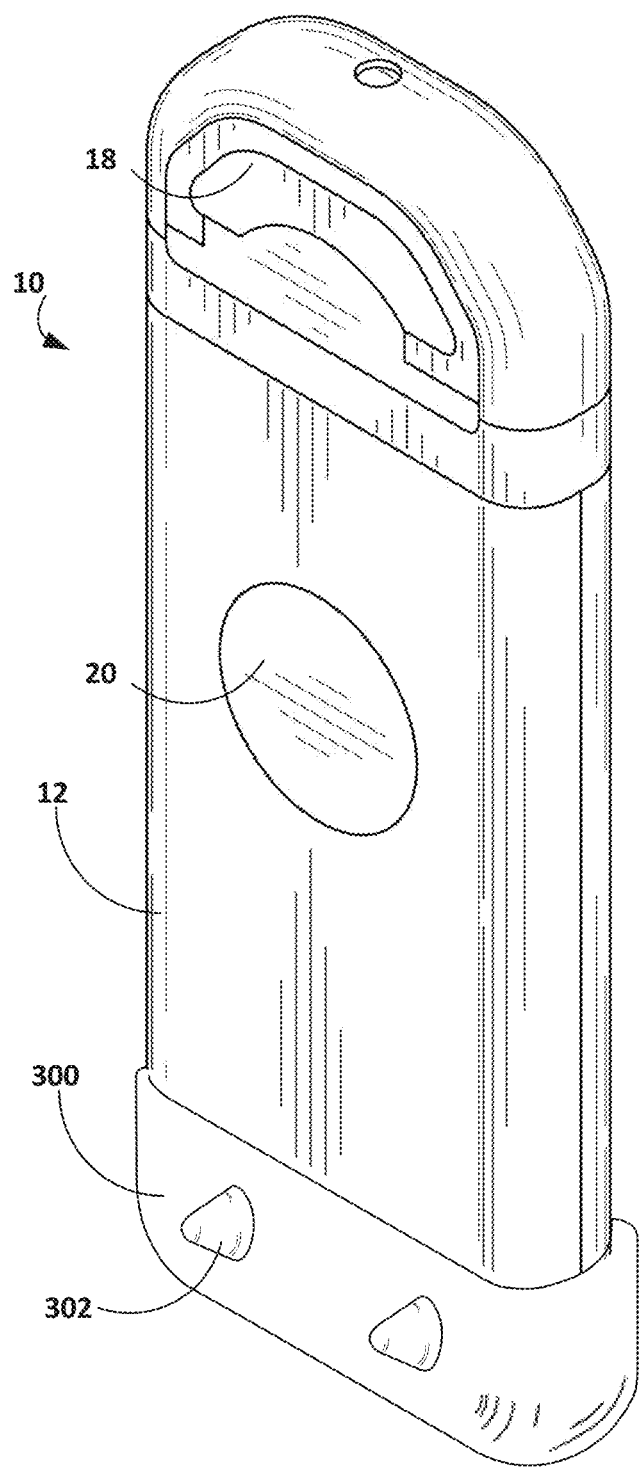
FIG. 8 is a schematic perspective view of a design for a mechanical anchor device that can be used with the disclosed neurostimulation device.

In some embodiments, the disclosed device 10 may include one or more mechanic anchors. FIG. 8 is a schematic perspective view of a design for a mechanical anchor device that can be used with the disclosed neurostimulation device 10. The anchor device main be in the form of a flexible anchor endcap (e.g., similar to flexible anchor endcap 210) that can fit over the distal end of housing 12. Endcap 300 may include one or more protrusion nubs 302 that extend away from the flexible endcap 300 of the anchor device. Protrusion nubs 302 are configured to dig into the surrounding tissue of the patient to create mechanical (e.g., friction) resistance to relative movement between device 10 and the surrounding tissue of the patient. In some embodiments protrusion nubs 302 may be conical shaped and composed of a flexible material the same as or similar to the material of the flexible endcap 300 or may be composed of a substantially rigid material. The size and shape of protrusion nubs 302 may be configured to enhance the resistive movement between the surrounding tissue and device 10 without causing physical irritation to the patient after implantation. Flexible endcap 300 may further include one or more suture points (not shown) such as those described above with respect to flexible anchor endcap 210.

Figure 9:
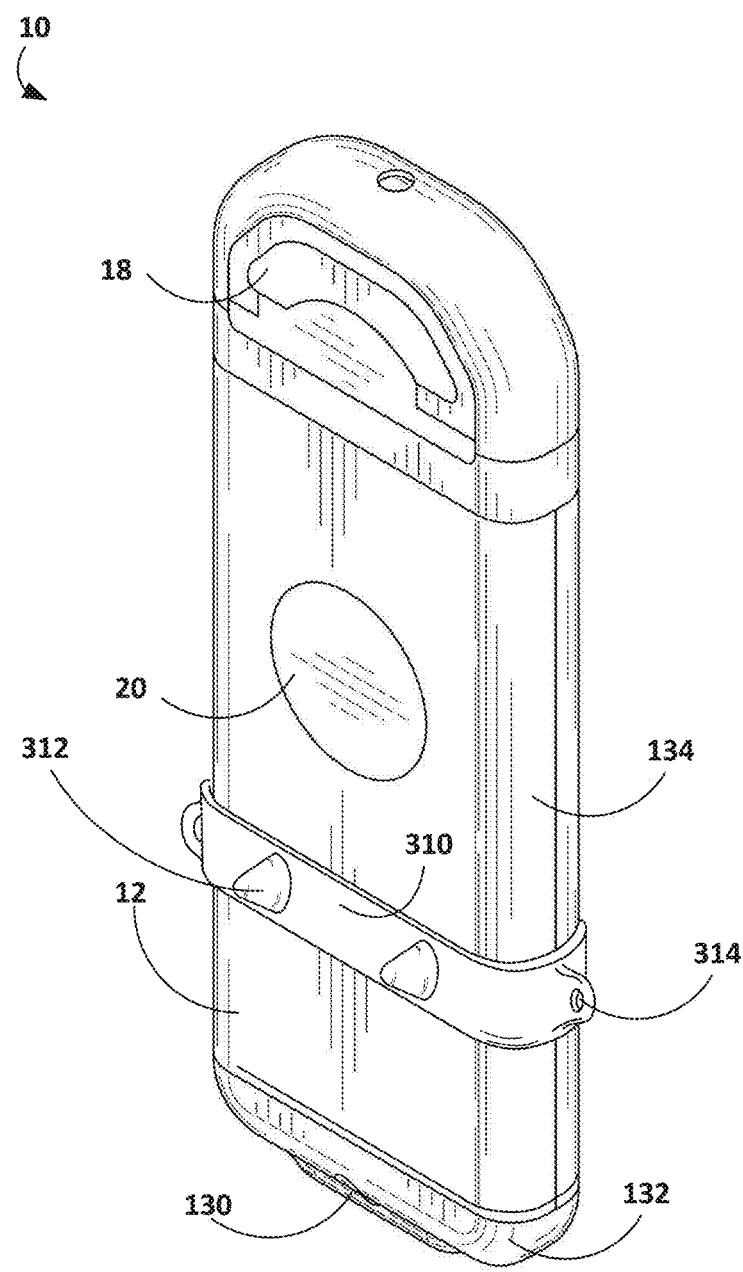
FIG. 9 is a schematic perspective view of another design for a mechanical anchor device that can be used with the disclosed neurostimulation device.

FIG. 9 is a schematic perspective view of another design for a mechanical anchor device that can be used with the disclosed neurostimulation device 10. The anchor device of FIG. 9 includes an anchor band 310 that includes one or more protrusion nubs 312 positioned on one or more sides of band 310 such as the side in common with electrodes 18 and 20. Protrusion nubs 312 may be substantially similar to nubs 302 and configured to extend away from the body of device 10 to engage the surrounding tissue of the patient and create mechanical (e.g., friction) resistance that inhibits relative movement between device 10 and the surrounding tissue of the patient. Anchor band 310 may be substantially similar to anchor band 220 described above and may further include one or more optional suture points 314, similar to suture points 222.

Figure 10:
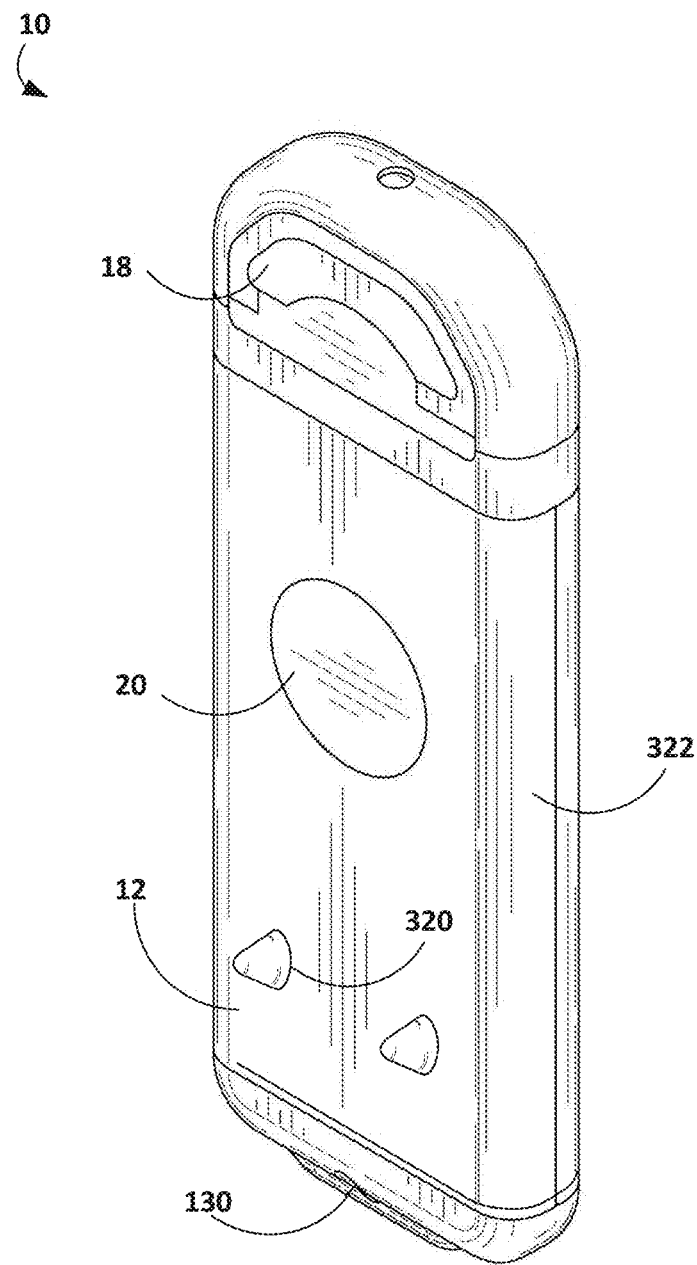
FIG. 10 is a schematic perspective view of another design for a mechanical anchor device that can be used with the disclosed neurostimulation device.

In yet another embodiment, the described protrusion nubs may be include with or on housing 12 of device 10. For example, FIG. 10 is a schematic perspective view of another design for a mechanical anchor device that includes one or more protrusion nubs 320 that can be used with the disclosed neurostimulation device. Protrusion nubs 320 may be integrally formed with hosing 12 of device 10 (e.g., defined by tubular body 322). If integrally formed with housing 12, protrusion nubs 320 may be composed of the same material as housing 12 and defined as part of the machining process used to manufacture housing 12. Alternatively, protrusion nubs 320 may be fabricated separately from housing 12 and fixably secured to housing 12 as part of the manufacturing process of device 10.

Protrusion nubs 320 may function substantially similar to the previously described protrusion nubs to create mechanical resistance that impedes relative movement between device 10 and the surrounding tissue of the patient. Protrusion nubs 320 may be included with one or more of the previously disclosed anchor devices.

In embodiments, device 10 may be provided as part of a kit, the kit including one or more of the disclosed endcaps, anchor bands, or anchor devices. A clinician may then select one or more of endcap, flexible band, or anchor device from the kit to be used with device 10 at the time of implant of device 10, according to the needs of a particular patient.

An advantage of the devices and methods described herein can be improved patient safety and satisfaction after implant. In contrast to other approaches, leadless neurostimulation device 10 does not require fascia layer 128 to be disturbed which may reduce risks affiliated with alternative procedures. Further, as device 10 is a unitary structure and can be hermetically sealed, the device is more robust than other lead-based stimulation units.

During operation, an electrical stimulation signal may be transmitted between primary electrode 18 and secondary electrode 20 through fascia layer 128. The electrical signal may be used to stimulate tibial nerve 102 which may be useful in the treatment of overactive bladder (OAB) symptoms of urinary urgency, urinary frequency and/or urge incontinence, or fecal incontinence.

EXAMPLES

Example 1—Minimum Threshold Current

Figure 11:
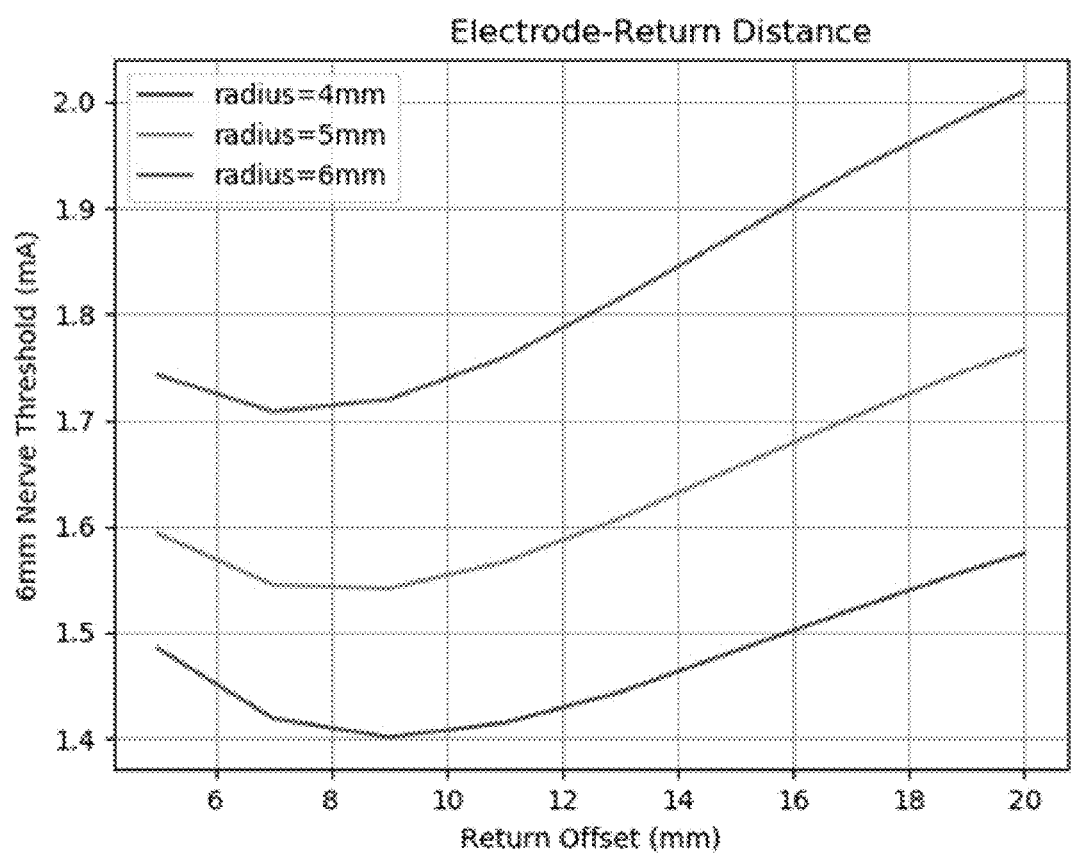
FIG. 11 is a plot showing examples of the minimum threshold level of current needed to observe a tibial nerve response based on a function of return offset in modelling studies using the disclosed leadless neurostimulation devices.

FIG. 11 is a plot showing examples of the minimum threshold level of electrical current needed to observe a tibial nerve response based on a function of the return offset (e.g., separation distance between primary electrode 18 and secondary electrode 20) in modelling studies. The studies also examined the minimal level of current needed to induce a simulated stimulation to a tibial nerve a select distance away as a function of secondary electrode size (e.g., circular radius). The minimum threshold was evaluated as the current required to stimulate a model of a single axon at the center of a tibial nerve (above the Y=0 axis) and a saphenous nerve (below the Y=0 axis) models.

Exemplary leadless neurostimulation devices were model based on the device of FIGS. 1A and 1B and the power componentry of an InterStim Micro implantable system for Sacral Neuromodulation from Medtronic. The size of the contact surface of the primary electrodes was approximately 21.3 mm$^2$. The size (radius) and positioning of the secondary electrode was modified for the study. The leadless neurostimulation devices were placed in computer models approximately 0.5 mm from a simulated fascia layer with approximately 6 mm separation to the tibial nerve.

As shown in FIG. 11, the minimum threshold current needed to obverse stimulation response to the tibial nerve occurred within the range of about 6 mm to about 13 mm of a return offset for the tested radii. For a secondary electrode size of about 4 mm (50 mm$^2$) a minimum threshold current of about 1.4 mA was observed at about a 9 mm offset. For a secondary electrode size of about 5 mm (79 mm$^2$) a minimum threshold current of about 1.55 mA was observed at about 8 mm offset. For a secondary electrode size of about 6 mm (113 mm$^2$) a minimum threshold current of about 1.7 mA was observed at about 7 mm offset. The smallest radii tested (4 mm) resulted in the lowest minimum threshold current (1.4 mA) but the largest return offset (9 mm).

Example 2—Offset and Depth Comparison

Figure 12A:
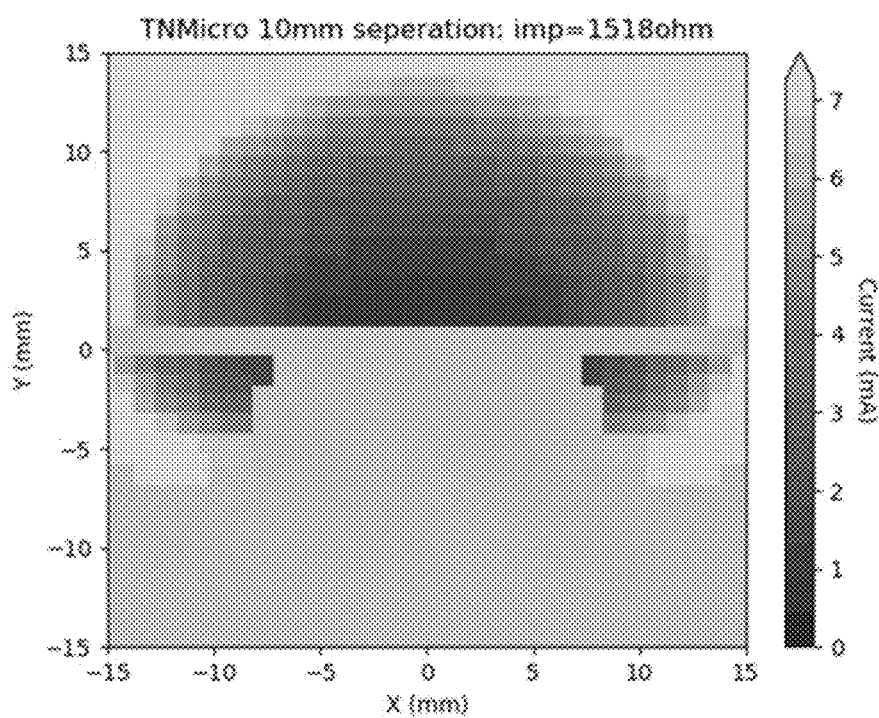
FIGS. 12A and 12B are plots showing modelling results of the effect of secondary electrode radius and the offset of the secondary electrode from the primary electrode in an example header on the stimulation threshold of a model of the tibial nerve located 6 mm away from the neurostimulation device.
Figure 12B:
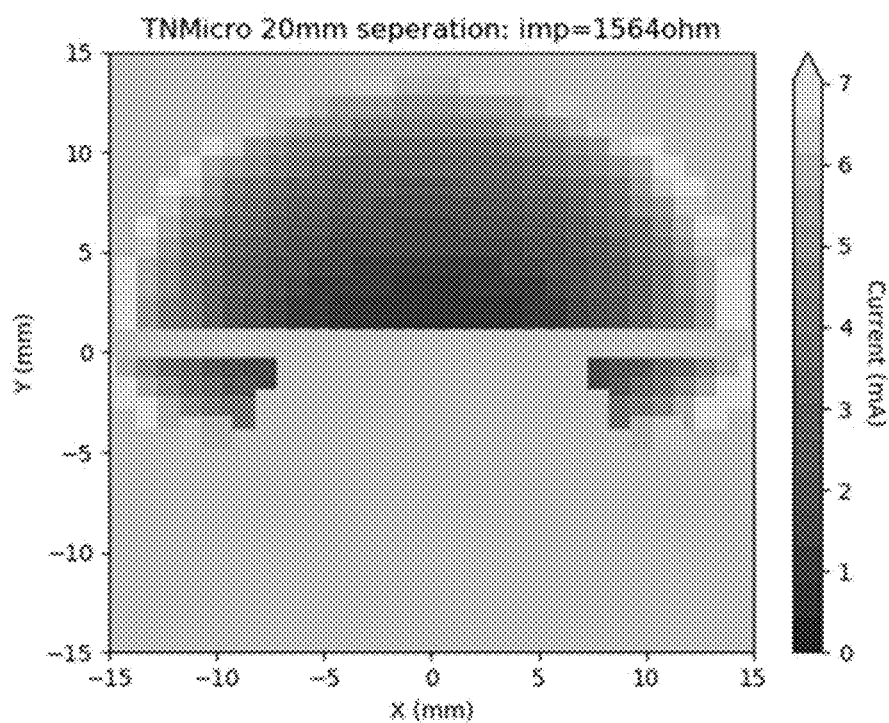

Simulations were conducted to examine the simulation depth as a function of the electrode offset (e.g., separation distance between primary and secondary electrodes) and stimulation voltage using modeling similar to Example 1. The size of the contact surface of the primary electrodes were approximately 21.3 mm$^2$ and the size of the secondary electrode was approximately 71 mm$^2$ (4.75 mm radius). The devices were tested at 10 mm and 20 mm electrode offsets. The leadless neurostimulation devices set in computer models approximately 0.5 mm from the fascia layer. FIGS. 12A and 12B are plots showing the threshold stimulation current in a cross-sectional view of the leg to capture the tibial nerve in the region above Y=0, and a cutaneous sensory nerve in the region below Y=0, for both 10 mm (FIG. 12A) and 20 mm (FIG. 12B) separation between the primary and secondary electrodes. The minimum threshold was evaluated as the current required to stimulate a model of a single axon at the center of a tibial nerve (above the Y=0 axis) and a saphenous nerve (below the Y=0 axis) models. The modeling demonstrated simulation obtainable within a radius of about 15 mm from the central axis of the device indicating that the disclosed device 12 may be useful in stimulating tibial nerves with deep or anterior tracks.

Figure 12C:
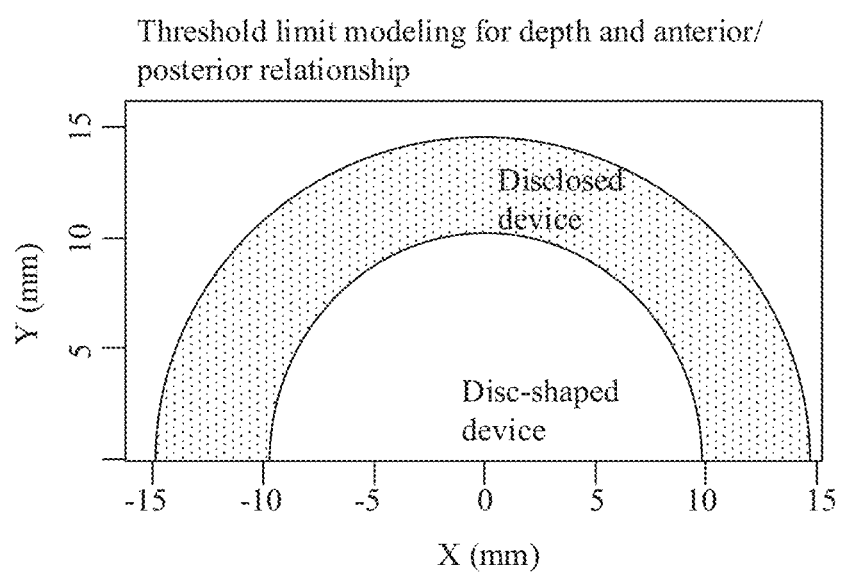
FIG. 12C is a plot showing modelling results of stimulation threshold limit for the disclosed device compared to a disc-shaped stimulation device for depth and anterior/posterior relationship.

The modeling was compared to simulation modeling for a disc-shaped stimulation device of 23 mm diameter and 2.2 mm thick. The disc stimulation device active electrode was modeled at about 12.5 mm$^2$ positioned at the center of the disc-shape and the return electrode was about 72.3 mm$^2$ and positioned at the perimeter edge of the side of the device. FIG. 12C is a plot showing modelling results FIG. 12C is a plot showing modelling results of stimulation threshold limit for the disclosed device compared to a disc-shaped stimulation device for depth and anterior/posterior relationship. The modeling demonstrated a notably reduced stimulation range (e.g., less than about 10 mm, e.g., 30% reduction in range) compared to the modeling of the present disclosed devices. It is believed that the reduction in operable range of the disc-shaped stimulation device may be due to the placement of the return electrode along the side of the device (e.g., not on the same side as the active electrode) as well as having the return electrode encircle the active electrode which negatively affect the possible pathway for the electrical stimulation. The modeling demonstrated that the disclosed device 12 may be useful in stimulating tibial nerves with deep or anterior tracks, particularly in comparison to disc-shaped stimulation devices.

Figure 13:
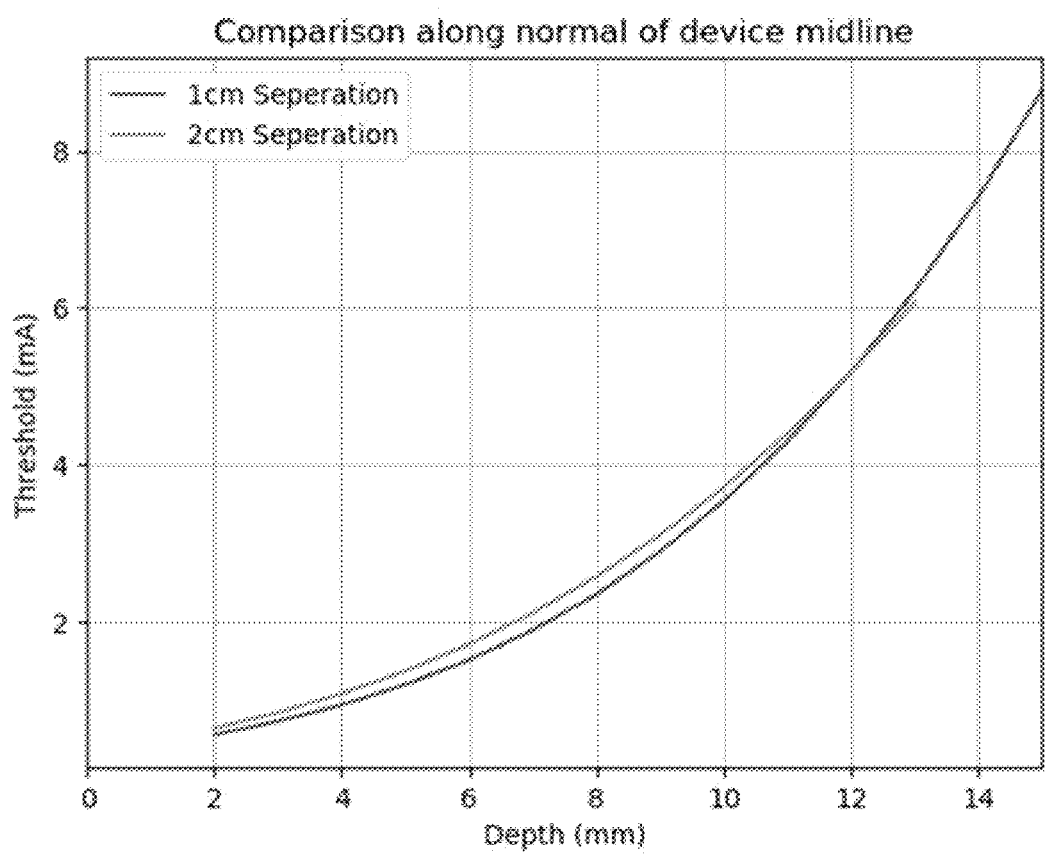
FIG. 13 is a plot showing the threshold current as a function of stimulation depth for both the 10 mm and 20 mm electrode offsets using a model of the disclosed leadless neurostimulation devices.

FIG. 13 shows the threshold current as a function of stimulation depth for both the 10 mm and 20 mm electrode offsets. The simulation depth was measured along the normal of the device midline. The results showed relatively similar results for both the 10 mm and 20 mm offset samples with slightly lower threshold values being determined for the 10 mm offset device at stimulation depths less than 12 mm.

Example 3: Impedance and Depth Examination

The electrode impedance and stimulation depth associated with the disclosed leadless neurostimulation devices were compared to a disc-shaped stimulation device using modeling similar to Example 1. The size of the contact surface of the primary electrode was approximately 21.3 mm$^2$ and the size of the secondary electrode was approximately 71 mm$^2$ (4.75 mm radius). The disc stimulation device was modeled to include a 23 mm diameter and 2.2 mm thick disc. The disc stimulation device active electrode was about 12.5 mm$^2$ positioned at the center of the coin-shape and the return electrode was about 72.3 mm$^2$ and positioned at the outer perimeter side of the device. Both devices were modeled approximately 0.5 mm from the fascia layer. The electrode impedance of the disclosed leadless neurostimulation devices between the active electrode and surrounding tissue were found to be significantly lower than that of the disc stimulation device (e.g., modeled at about 1500 ohms or less compared to about 2100 ohms for the disc stimulation device). The comparatively lower electrode impedance can allow for a higher current amplitude to be achieved for the same voltage, as well as better depth penetration. The comparatively lower electrode impedance for the disclosed leadless electrodes may contribute to the device's ability to stimulate nerves over a larger area (laterally and depth) compared to the modeled disc-shaped device using comparable stimulation output.

Animal tests were also conducted to assess the practical electrode impedance for representative neurostimulation devices of the disclose invention. Exemplary leadless neurostimulation devices were prepared by using an InterStim Micro implantable system for Sacral Neuromodulation from Medtronic that was modified to include the disclosed header unit 14 and secondary electrode 20. The device was implanted in ovine models approximately 0.5 mm from the fascia layer with approximately 6 mm separation to the tibial nerve. The observed electrode impedance was surprisingly low at values of about 300 ohms. (e.g., approximately 316±130 ohms for the 10 mm separation and approximately 282±85 ohms for the 20 mm separation).

Figure 14:
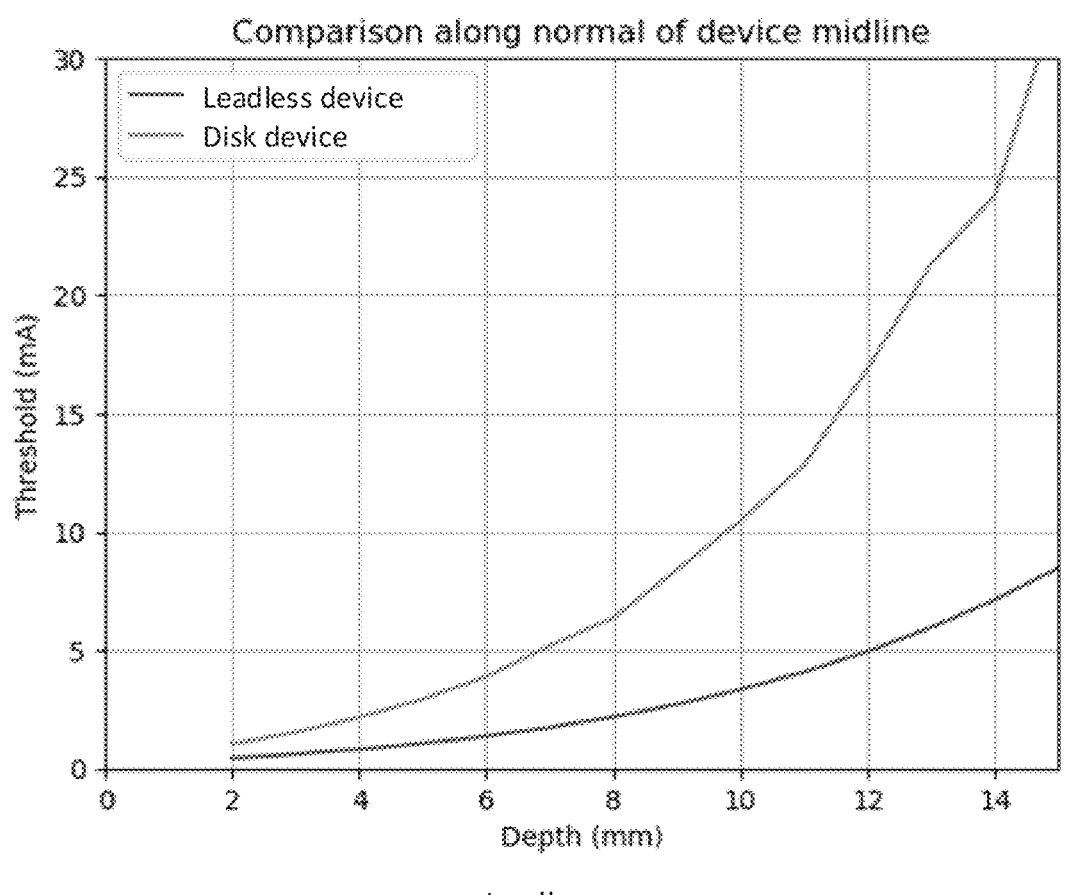
FIG. 14 is a comparative plot of models showing the threshold stimulation current as a function of stimulation depth for a comparative disc stimulation device and the disclosed leadless neurostimulation device.

The threshold stimulation current as a function of stimulation depth was also modelled and compared between the disc stimulation device and the disclosed leadless neurostimulation device, which are plotted in FIG. 14. The disclosed leadless neurostimulation devices demonstrated a significant improvement in reducing the minimum threshold current to obtain tibial stimulation with increasing stimulation depth.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer). Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

What is claimed is:

1. A leadless neurostimulation device comprising:
   a header unit comprising:
      at least one primary electrode having a contact surface that defines an external surface of the leadless neurostimulation device, the at least one primary electrode comprising a cathode;
   a housing comprising a secondary electrode positioned on the same side of the leadless neurostimulation device as the at least one primary electrode, the secondary electrode comprising an anode; and
   processing circuitry within the housing configured to deliver electrical stimulation therapy, the processing circuitry electrically coupled to the at least one primary electrode and secondary electrode and are configured to transmit an electrical stimulation signal between the cathode in the header unit and the anode on the housing to provide the electrical stimulation therapy to a target nerve of a patient.

2. The leadless neurostimulation device of claim 1, wherein the header unit further comprises an outer housing that forms a side of the header unit opposite of the contact surface of the primary electrode; and
   a dielectric mount that receives at least a portion of the at least one primary electrode and at least partially surrounds the at least one primary electrode.

3. The leadless neurostimulation device of claim 2, wherein the dielectric mount is configured to electrically insulate the at least one primary electrode from the outer housing, the dielectric mount being received and fixed within a recessed portion of the outer housing.

4. The leadless neurostimulation device of claim 1, wherein the header unit comprises two to four primary electrodes each having a contact surface that forms an exterior surface of the header unit.

5. The leadless neurostimulation device of claim 4, wherein at least one of the two to four primary electrodes is configured to sense a relative location of a tibial nerve prior to delivery of stimulation therapy.

6. The leadless neurostimulation device of claim 1, wherein the contact surface of the at least one primary electrode is about 20 mm$^2$ to about 25 mm$^2$.

7. The leadless neurostimulation device of claim 1, wherein the at least one primary electrode and the secondary electrode define a separation distance of about 10 mm to about 20 mm.

8. The leadless neurostimulation device of claim 1, wherein the secondary electrode defines a contact surface area of about 40 mm$^2$ to about 120 mm$^2$.

9. The leadless neurostimulation device of claim 1, further comprising a dielectric coating or a dielectric surface treatment that electrically insulates at least one primary electrode from the secondary electrode along an exterior surface of the device.

10. The leadless neurostimulation device claim 9, wherein a boundary defined by the dielectric coating or the dielectric surface treatment defines the secondary electrode.

11. The leadless neurostimulation device of claim 1, wherein the device defines a total volume of about 0.5 cubic centimeters (cc) to about 5 cc.

12. The leadless neurostimulation device of claim 1, further comprising a mounting plate, wherein the housing is coupled to a first side of the mounting plate and the header unit is coupled to a second side of the mounting plate.

13. The leadless neurostimulation device of claim 1, wherein the at least one primary electrode is sized and shaped to have an impedance of about 200 ohms to about 2,000 ohms when the leadless neurostimulation device is implanted.

14. A leadless neurostimulation device comprising:
   a header unit comprising:
      at least one primary electrode having a contact surface that defines an external surface of the leadless neurostimulation device, the at least one primary electrode comprising a cathode;
   a housing comprising a secondary electrode positioned on the same side of the leadless neurostimulation device as the at least one primary electrode, the secondary electrode comprising an anode; and
   a suture anchor device comprising at least one suture point for securing the leadless neurostimulation device to patient tissue,
      wherein the leadless neurostimulation device includes processing circuitry electrically coupled to the at least one primary electrode and the secondary electrode and are configured to transmit and receive, respectively, an electrical stimulation signal between the cathode and the anode to provide electrical stimulation therapy to a target nerve of a patient.

15. The leadless neurostimulation device of claim 14, wherein the housing comprises a tubular body and an endcap coupled together, wherein the endcap comprises the suture anchor device.

16. The leadless neurostimulation device of claim 14, wherein the suture anchor device comprises a flexible endcap configured to receive a portion of the housing.

17. The leadless neurostimulation device of claim 14, wherein the suture anchor device comprises at least one suture point arranged flush with a side of the suture anchor device that is on the same side of the leadless neurostimulation device as the secondary electrode.

18. The leadless neurostimulation device of claim 14, wherein the leadless neurostimulation device or the suture anchor device further comprises at least one protrusion nub configured to create mechanical resistance that impedes relative movement between wherein the leadless neurostimulation device and the patient tissue when implanted.

19. A leadless neurostimulation device comprising:
   a header unit comprising:
      at least one primary electrode having a contact surface that defines an external surface of the leadless neurostimulation device;
      an outer housing that forms a side of the header unit opposite of the contact surface of the primary electrode; and
      a dielectric mount that receives at least a portion of the at least one primary electrode and at least partially surrounds the at least one primary electrode, the dielectric mount being configured to electrically insulate the at least one primary electrode from the outer housing, the dielectric mount being received and fixed within a recessed portion of the outer housing;
   a housing comprising a secondary electrode positioned on the same side of the leadless neurostimulation device as the at least one primary electrode, the at least one primary electrode and the secondary electrode being configured to transmit an electrical stimulation signal therebetween to provide electrical stimulation therapy to a tibial nerve of a patient,
   a dielectric coating or a dielectric surface treatment that electrically insulates at least one primary electrode from the secondary electrode along an exterior surface of the device, wherein a boundary defined by the dielectric coating or the dielectric surface treatment defines the secondary electrode; and
   a suture anchor device comprising at least one suture point for securing the leadless neurostimulation device to patient tissue,
   wherein the at least one primary electrode and the secondary electrode define a separation distance of about 10 mm to about 20 mm, and
   wherein the leadless neurostimulation device defines a total volume of about 1.5 cubic centimeters (cc) to about 3.5 cc.

20. The leadless neurostimulation device of claim 19, wherein the housing comprises a tubular body and an endcap coupled together, wherein the endcap comprises the suture anchor device.

21. The leadless neurostimulation device of claim 19, wherein the suture anchor device comprises a flexible endcap configured to receive a portion of the housing.

22. The leadless neurostimulation device of claim 19, wherein the contact surface of the at least one primary electrode is about 20 $mm^2$ to about 25 $mm^2$, and further wherein the secondary electrode defines a contact surface area of about 40 $mm^2$ to about 120 $mm^2$.

23. A leadless neurostimulation device comprising:
   a header unit comprising:
      at least one primary electrode having a contact surface that defines an external surface of the leadless neurostimulation device;
      an outer housing that forms a side of the header unit opposite of the contact surface of the primary electrode; and
      a dielectric mount that receives at least a portion of the at least one primary electrode and at least partially surrounds the at least one primary electrode, wherein the dielectric mount is configured to electrically insulate the at least one primary electrode from the outer housing, the dielectric mount being received and fixed within a recessed portion of the outer housing; and
   a housing comprising a secondary electrode positioned on the same side of the leadless neurostimulation device as the at least one primary electrode, wherein the at least one primary electrode and the secondary electrode are configured to transmit an electrical stimulation signal therebetween to provide electrical stimulation therapy to a target nerve of a patient.

* * * * *